(12) United States Patent
Pustan et al.

(10) Patent No.: US 9,914,638 B2
(45) Date of Patent: Mar. 13, 2018

(54) SENSOR PACKAGE

(71) Applicant: Sensirion AG, Stafa (CH)

(72) Inventors: David Pustan, Zurich (CH); Werner Hunziker, Stafa (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 14/993,738

(22) Filed: Jan. 12, 2016

(65) Prior Publication Data
US 2016/0200564 A1    Jul. 14, 2016

(30) Foreign Application Priority Data
Jan. 14, 2015   (EP) ................................ 15000074

(51) Int. Cl.
| | |
|---|---|
| *B81B 3/00* | (2006.01) |
| *B81C 1/00* | (2006.01) |
| *H01L 23/31* | (2006.01) |
| *G01N 33/00* | (2006.01) |

(52) U.S. Cl.
CPC .......... *B81B 3/0081* (2013.01); *B81C 1/0069* (2013.01); *B81C 1/00158* (2013.01); *G01N 33/0009* (2013.01); *B81B 2201/0278* (2013.01); *B81B 2203/0127* (2013.01); *B81B 2207/098* (2013.01); *H01L 23/3107* (2013.01); *H01L 2924/0002* (2013.01)

(58) Field of Classification Search
CPC .......... B81B 3/0081; B81B 2203/0127; B81B 2207/098; B81C 1/0069; B81C 1/00158; G01N 33/0009; H01L 23/31; H01L 23/315; H01L 23/564

USPC ............ 257/414-417, 420, 467, 712; 438/48
See application file for complete search history.

(56) References Cited

U.S. PATENT DOCUMENTS

| | | |
|---|---|---|
| 5,296,738 A | 3/1994 | Freyman et al. |
| 5,612,576 A | 3/1997 | Wilson et al. |
| 5,721,450 A | 2/1998 | Miles |
| 6,242,802 B1 | 6/2001 | Miles et al. |
| 6,490,166 B1 | 12/2002 | Ramalingam et al. |
| 6,690,569 B1 | 2/2004 | Mayer et al. |
| 6,809,407 B2 | 10/2004 | Shimizu |
| 7,906,859 B2 | 3/2011 | Yoshioka et al. |
| 8,522,426 B2 | 9/2013 | Dennis et al. |
| 2007/0218585 A1* | 9/2007 | Robert ................ B81C 1/00285 438/106 |

(Continued)

FOREIGN PATENT DOCUMENTS

| | | |
|---|---|---|
| DE | 102008039068 | 8/2007 |
| DE | 202011051190 | 1/2012 |

(Continued)

OTHER PUBLICATIONS

Die Attach Adhesive Solutions, A1 Technologies Inc., Oct. 30, 2014, pp. 3-13.

*Primary Examiner* — Johannes P Mondt
(74) *Attorney, Agent, or Firm* — Cooper & Dunham LLP

(57) ABSTRACT

A sensor package comprises a carrier comprising a through hole, and a sensor chip with a front side and a back side and a recess in the back side. The sensor chip is attached to the carrier with its back side facing the carrier by means of an attachment layer thereby defining a first area of the carrier the sensor chip rests on and a second area of the carrier facing the recess. The through hole is arranged in the first area of the carrier.

13 Claims, 3 Drawing Sheets

(56) References Cited

U.S. PATENT DOCUMENTS

| | | |
|---|---|---|
| 2013/0056703 A1 | 3/2013 | Elian et al. |
| 2013/0202012 A1* | 8/2013 | Peroulis .................. G01K 7/34 |
| | | 374/184 |
| 2014/0008737 A1* | 1/2014 | Koduri ................ G01P 15/0802 |
| | | 257/415 |
| 2014/0070411 A1 | 3/2014 | Okada |
| 2014/0312514 A1 | 10/2014 | Yasunaga et al. |
| 2015/0362451 A1 | 12/2015 | Hunziker et al. |

FOREIGN PATENT DOCUMENTS

| | | |
|---|---|---|
| JP | 5269990 | 8/2013 |
| WO | 0142776 | 6/2001 |
| WO | 2006114005 | 11/2006 |
| WO | 2010140545 | 12/2010 |

* cited by examiner

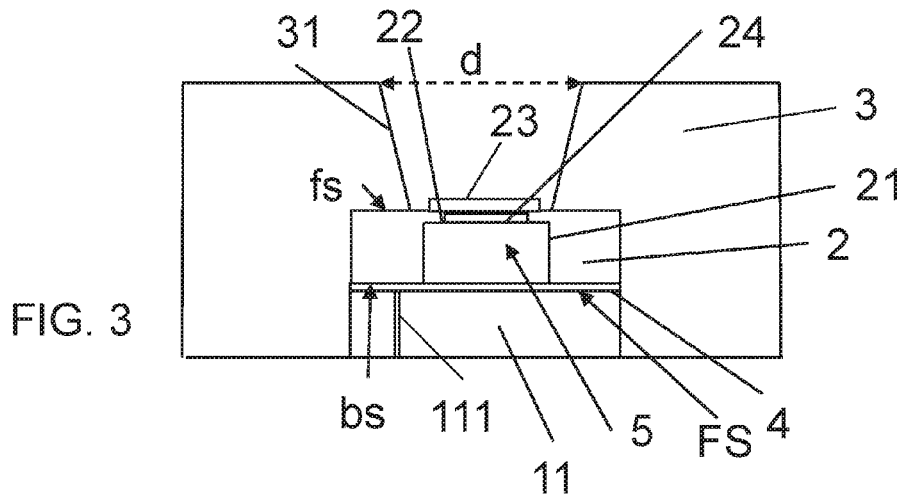
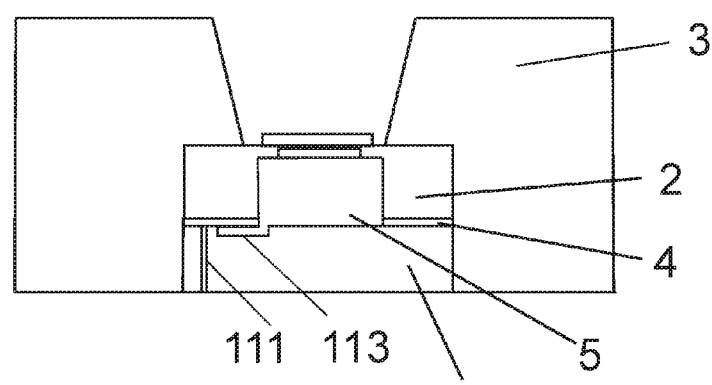
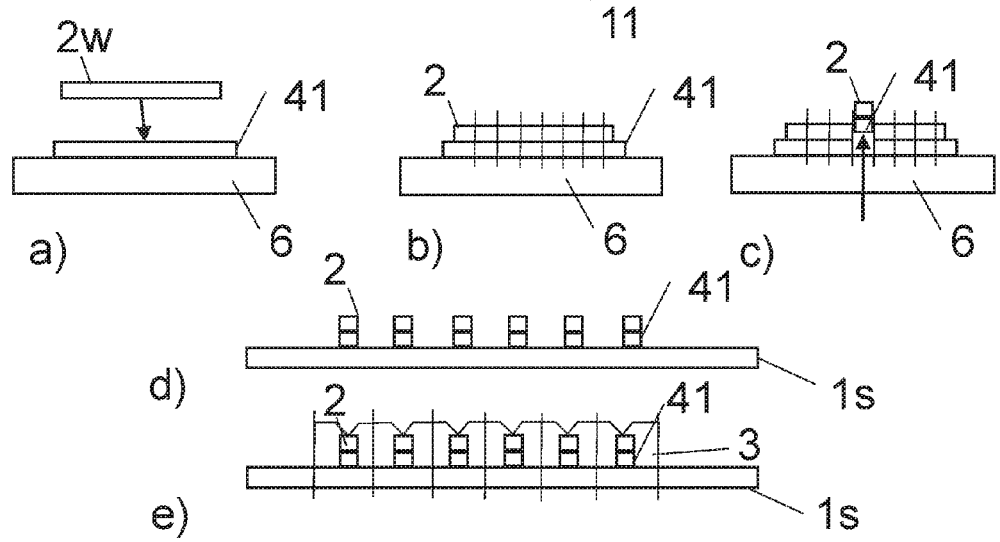
FIG. 5

SENSOR PACKAGE

CROSS REFERENCE TO RELATED APPLICATION

This application claims the priority of European Patent Application No. 15000074.3, filed Jan. 14, 2015, the disclosure of which is incorporated herein by reference in its entirety.

TECHNICAL BACKGROUND

An increasing number of sensors are integrated into semiconductor chips. Such a sensor chip may be placed on a carrier such as a die pad, and possibly be encapsulated.

In some applications, the sensor chip is thinned from a back side of the sensor chip for building a thin membrane that is thermally isolated versus the rest of the sensor chip. This may serve the operation of a sensitive element on or in the membrane, for example, in particular when the sensitive element is provided for sensing a temperature or otherwise is sensitive to temperature, or, for example, when a heating operation is required during measuring or manufacturing which heat is not desired to migrate elsewhere to the chip but is desired to remain locally confined, e.g. in the membrane.

When such a sensor chip is mounted to a die pad with its back side facing the die pad, a cavity is generated between the sensor chip and the die pad in view of the recess in the sensor chip. In such arrangement, the membrane of the sensor chip lowers the total mechanical resistance of the sensor package, and the underlying cavity may promote an accumulation of moisture, for example, during manufacturing, shipment or handling. In particular, moisture may be absorbed by an encapsulation of the sensor chip containing organic material, e.g. plastics, if applicable, which moisture may be released into the cavity in response to elevated temperatures. During assembly, for example, a solder reflow process may induce elevated temperatures to the entire sensor package including the encapsulation if any. However, elevated temperatures may also be induced from external, or from internal, wherein during operation, for example, a heater may induce elevated temperatures if applicable. Irrespective of the source of heating, such elevated temperature may result in a vapor pressure increase inside the cavity, and in a plastic encapsulation of the sensor chip if applicable. Such moisture uptake may finally lead to delamination of material interfaces and/or to cracks in the sensor package which is also referred to as "popcorn" phenomenon.

For moisture/reflow sensitive components such as plastic-encapsulated surface mounted devices and other packages made with moisture-permeable materials, a moisture sensitivity level is determined by tests and a resulting classification determines storage conditions, packing, handling and timing specifications for the product at the manufacturer and the customer. In case the sensitivity of a sensor package to moisture can be reduced and less stringent moisture sensitivity levels can be achieved, packing requirements may be reduced and the handling of the sensor package may be facilitated. However, drilling a hole in the die pad underneath the cavity does not seem to solve the problem given that such hole provides access to the cavity and the membrane in the following which may allow dust, flux, PCB coating material, assembly chemicals, etc. enter the cavity e.g. during assembly of the sensor package itself, e.g. during dicing, handling, testing, etc., during shipment, during assembly on a PCB at costumer side, and during whole operating lifetime.

Hence, it is desired to provide a sensor package that is less prone to a vapor pressure increase in the cavity.

DISCLOSURE OF THE INVENTION

According to a first aspect of the invention, a sensor package is provided comprising a sensor chip with a front side and a back side, and with a recess in the back side. The sensor chip is attached to a carrier by means of an attachment layer with the back side facing the carrier thereby defining a first area of the carrier the sensor chip rests on and a second area of the carrier facing the recess. A through hole is provided in the carrier and is arranged in its first area. The through hole preferably is covered by the attachment layer and preferably serves as venting hole.

The carrier is meant to carry the sensor chip, which sensor chip is attached to the carrier. In this context, it is preferred that the carrier is a flat plate-like support. Preferably, the carrier is a die pad. However, all embodiments relating to the die pad in the following may also be applied to a different kind of carrier. In a preferred embodiment, the die pad is made from metal, and specifically is part of a lead frame structure.

At first glance, there is no direct channel between a cavity defined by the recess and the carrier on the one hand and the through hole on the other hand since the through hole is arranged offset from the recess. Instead, the attachment layer seals in between the sensor chip and the carrier. The attachment layer in one embodiment comprises an adhesive, such as epoxy material. At high temperatures, however, the attachment layer softens and allows a highly compressed gas caused by vapor pressure in the cavity to leak out from the cavity between the attachment layer and the sensor chip, or between the attachment layer and the carrier, and/or through the attachment layer to the venting hole. After pressure relief such channel through the attachment layer may close again. Without such a pressure relief, the membrane may risk to break at a certain loading. Hence, the attachment layer serves as a temperature and/or pressure dependent venting medium for releasing the cavity from excess pressure. On the other hand, the lack of a direct channel between the cavity and the through hole prevents solder, gas or water from intruding into the cavity, which otherwise may happen, for example, during manufacturing including assembly. At the same time, the cavity is protected from contamination, induced by flux during a solder reflow process at the customer, for example.

Hence, the present idea allows pressure balancing and removal of moisture from the cavity and thereby may achieve a lowered moisture sensitivity level (e.g. MSL-1 instead of MSL-3). This is achieved by adding the venting hole in the carrier next to the cavity or next to a groove, preferably in form of a half etched channel in the carrier, which connects to the cavity and leads next to the venting hole in the carrier. The carrier preferably is part of a lead frame structure made from an electrically and thermally conducting material, such as metal. Preferably, the sensor package is a QFN package (Quad Flat No-leads).

The sensor chip, also referred to as die, may contain a semiconductor substrate, such as a silicon substrate, into which semiconductor substrate a processing circuit preferably is integrated. Layers, such as CMOS layers may be provided for building the integrated processing circuit. The sensor chip has a front side and a back side, wherein a sensitive layer preferably is arranged at the front side. The sensitive layer may be arranged on top of or integrated in the semiconductor substrate or on top of or integrated in a layer, such as one of the CMOS layers, and preferably on or in a membrane of the sensor chip that spans the cavity. In case an integrated processing circuit is provided in the sensor chip, the sensitive layer may be connected thereto for pre-processing signals from the sensitive layer in the integrated processing circuit.

Specifically, the sensitive layer may contain a metal oxide material, and in particular a semiconducting metal oxide material. A metal oxide material generally may include one or more of tin oxide, zinc oxide, titanium oxide, tungsten oxide, indium oxide and gallium oxide. Such metal oxides may be used for the detection of analytes such as VOCs, carbon monoxide, nitrogen dioxide, methane, ammonia or hydrogen sulphide. Metal oxide sensors are based on the concept that gaseous analytes interact with the metal oxide layer at elevated temperatures of the sensitive layer in the range of more than 100° Celsius, and specifically between 250° C. and 350° Celsius. As a result of the catalytic reaction, the conductivity of the sensitive layer may change which change can be measured. The sensor therefore may be a gas sensor.

In another embodiment, the sensitive layer may comprise a polymer that in one embodiment may be sensitive to $H_2O$ such that the sensor may be a humidity sensor. A capacity or a resistance of such polymer layer may be measured for deriving information as to the gas that may interact with the sensitive layer.

In another embodiment, the sensitive layer may comprise temperature sensing means for detecting a flow of a fluid, such as the flow of a gas or the flow of a liquid.

In addition, a heater can be provided, and preferably is arranged on or in the membrane, for supporting a measurement by the sensitive layer and/or for supporting a manufacturing of the sensor package. In one embodiment, the heater is required for heating the sensitive layer prior to and/or during a gas measurement. This may be the case, for example, when the sensitive layer contains metal oxide material. In another embodiment, the heater may alternatively or additionally be used for annealing the sensitive layer after having applied a sensitive material to the sensor chip for building the sensitive layer from. This may be the case when the sensitive layer comprises a polymer, and/or when the sensitive layer is made from a material comprising metal oxide. In a third embodiment, the heater may be used for heating the fluid passing the sensitive layer for generating a gradient in temperature upstream and a downstream of the heater which can be measured by the temperature means.

The membrane may be provided to achieve thermal insulation. In a preferred embodiment, the membrane is manufactured by etching, such as dry-etching or wet-etching, or otherwise removing material from the back side of the sensor chip, such as bulk substrate material, thereby generating a recess in the back side of the sensor chip. The remaining material of the sensor chip above the recess forms the membrane which may consist of CMOS layers and/or parts of the bulk substrate material.

The carrier may have a footprint approximately equal to a footprint of the sensor chip. The through hole in the carrier may be fabricated subject to the material of the carrier and/or the carrier in general, e.g. by etching, piercing, laser drilling, mechanical drilling, etc. Preferably, contact pads are provided for electrically contacting the sensor chip. The contact pads are preferably made from the same material as the carrier in case of being separate from the carrier and in case of being made from metal, and are preferably arranged in the same plane as the carrier. In a different embodiment, the carrier may comprise the contact pads. The contact pads are exposed to the environment as pins for electrical contact. In one embodiment, the contact pads and the carrier represent a lead frame structure. The contact pads may be represented by electrically conducting platforms or leads electrically isolated from each other.

A molding compound may be applied to a lead frame structure/sensor chip combination. The molding compound preferably comprises plastics and preferably is an epoxy with filler particles which filler particles e.g. may be glass. The molding compound at least partially encloses and/or encapsulates the sensor chip. Preferably, an opening is provided in the molding compound for allowing a gas a variable of which is to be measured to access the sensitive layer of the sensor chip. The molding compound encapsulates and as such covers the sensor chip essentially except for the sensitive layer such that any outgassing from the sensor chip itself, from adhesives between the sensor chip and the carrier, or from the carrier itself etc. does not have any impact on the measurement.

In an alternate embodiment, a printed circuit board (PCB) may act as carrier Here, the sensor chip is attached to a front side of the printed circuit board, while the contact pads may be formed by metallizations on a back side of the printed circuit board which additionally requires vias through the printed circuit board for connecting to the contact pads. Instead of a printed circuit board, another carrier such as a ceramic substrate or a glass substrate may be used.

According to a further aspect of the present invention, a method is provided for manufacturing a sensor package. A sensor chip is manufactured with a front side, a back side and a recess in the back side. A through hole is manufactured in a carrier which carrier later on carries the sensor chip. The sensor chip is attached to the carrier with its back side facing the carrier by means of an attachment layer such that the through hole is located in a first area of the carrier the sensor chip rests on. The through hole preferably is covered by the attachment layer. This may in particular be the case if the carrier is attached to the sensor chip by a die attach film as attachment layer. Here, a second area of the carrier which is defined as area facing the recess may also be covered by the attachment layer. In a different embodiment, and preferably if the carrier is attached to the sensor chip by a wafer backside coating as attachment layer, the attachment layer may be structured and therefore only cover the first area excluding the through hole and excluding the second area. Hence, in this embodiment the attachment layer may be understood as having cut-outs for the second area and for the through hole.

Other advantageous embodiments of the gas sensor package are listed in the dependent claims as well as in the description below and shall be considered as embodiments to both the arrangement and the method.

BRIEF DESCRIPTION OF THE DRAWINGS

Embodiments of the present invention, aspects and advantages will become apparent from the following detailed description thereof. Such description makes reference to the annexed drawings, wherein the figures show:

FIG. 3 a cross-sectional view of the sensor package of FIG. 1 along line A-A';

FIG. 4 a cross-sectional view of the sensor package of FIG. 2 along line A-A';

FIG. 5 diagrams illustrating a method for manufacturing a sensor package according to an embodiment of the present invention;

DETAILED DESCRIPTION OF THE DRAWINGS

Figure 1:
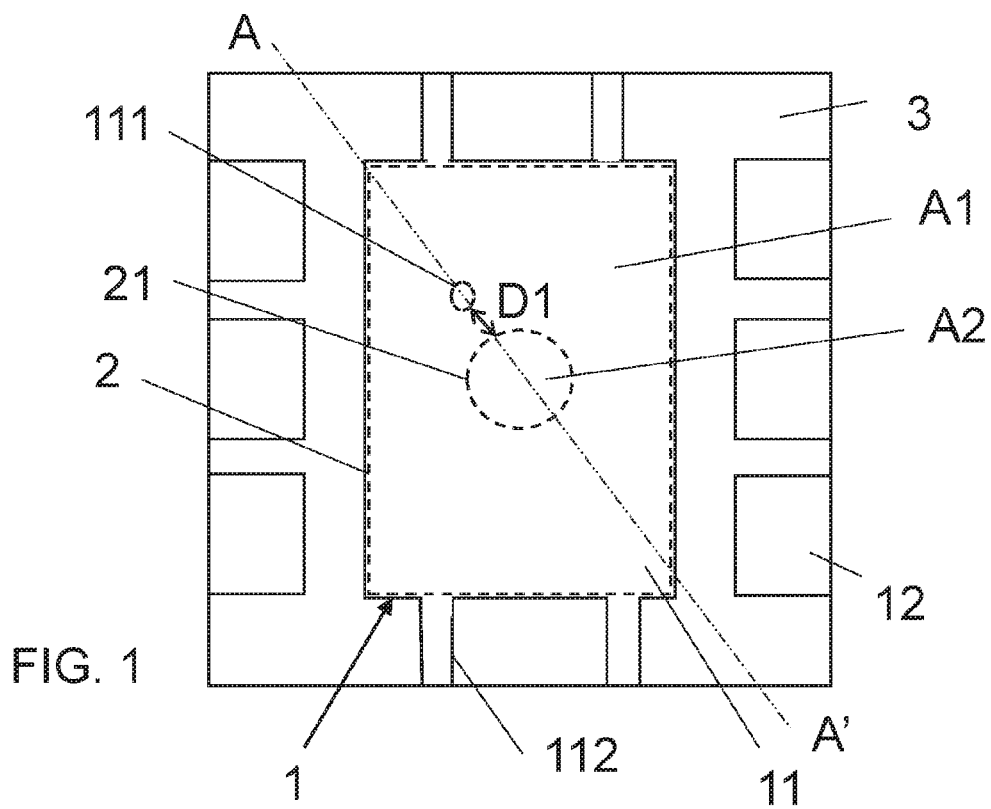
FIG. 1 a transparent top view on a sensor package according to an embodiment of the present invention.

In the drawings, same elements are referred to by the same reference signs.

FIG. 1 illustrates a transparent top view on a sensor package according to an embodiment of the present invention.

In between two rows of contact pads 12, a carrier in form of a die pad 11 is provided which serves as a support for a sensor chip 2 indicated in dashed lines. The die pad 11 is of rectangular shape and may in a different embodiment have one flattened corner at least on its bottom side, e.g. manufactured by etching half the thickness of the die pad 11, which may serve as an optical and/or mechanical encoding for an orientation of the sensor package. The contact pads 12 and the die pad 11 are mechanically linked by a molding compound 3.

The sensor chip 2 has a recess in its back side referred to by 21 and illustrated by a dashed circle. Given that the sensor chip 2 rests with its back side on the die pad 11, a first area A1 of the die pad 11 is defined as the area the sensor chip 2 actually rests on, i.e. is in contact with the die pad 11 via an attachment layer to be introduced later on. A second area A2 instead is defined as area of the die pad that faces the recess 21 of the sensor chip 2.

A through hole 111 is provided in the die pad 11 which extends through an entire thickness of the die pad 11. The through hole 111 is arranged in the first area A1 of the die pad 11, i.e. where the sensor chip 2 rests on the die pad 11. Its area is referred to by A3 which area A3 resides within the first area A1.

The sensor chip 2 is attached to the die pad 11 by means of an attachment layer. Preferably, the attachment layer is an adhesive film that permanently sticks the sensor chip 2 to the die pad 11. Hence, the attachment layer is arranged between the die pad 11 and the back side of the sensor chip 2. The attachment layer is not explicitly shown in FIG. 1 for serving a better illustration. There may be different embodiments as to which area of the die pad 11 the attachment layer covers: In a first variant, the attachment layer covers area A1 including area A3, and covers area A2. In a second variant, the attachment layer solely covers area A1 including area A3 but not area A2. In a third variant, the attachment layer solely covers area A1 excluding areas A2 and A3.

A distance D1 between the through hole 111 and the recess 21 preferably is less than 250 µm. During operation, a cavity defined by the recess 21 in the sensor chip 2 and the die pad 11 may suffer from elevated pressure, contaminated gas etc. Hence the through hole 111 offers an exit for gas in the cavity. However, the only way to get from the cavity to the through hole 111 is by overcoming the attachment layer between the recess 21 and the through hole 111. The material of the attachment layer and its dimension may be chosen or designed to make this venting channel become more or less resistive to a gas flow.

Figure 2:
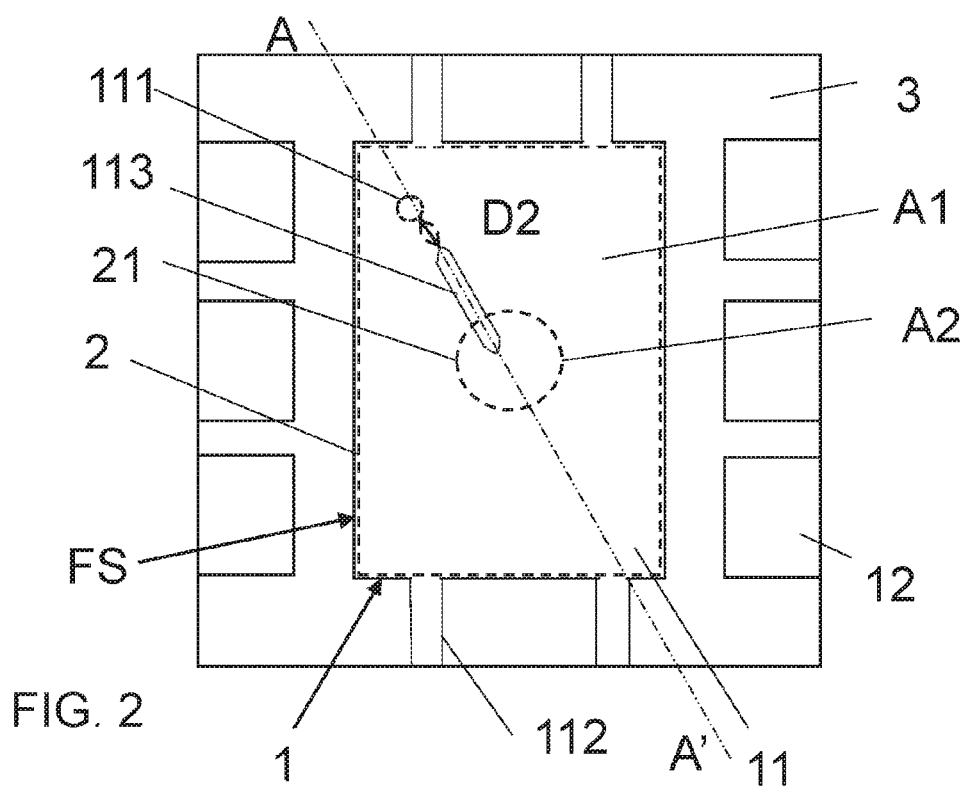
FIG. 2 a transparent top view on a sensor package according to another embodiment of the present invention.

FIG. 2 illustrates a transparent top view on a sensor package according to another embodiment of the present invention. In contrast to the embodiment of FIG. 1, the through hole 111 now is arranged at a greater distance from the recess 21. However, a groove 113 is provided, which may be considered a groove in a front side FS of the die pad 11, e.g. generated by etching the thickness of the die pad e.g. half way down. Hence, the groove 113 may be understood as an extension of the cavity towards the through hole 111. In the present example, the groove reaches into the second area A2. However, the groove 113 terminates prior to reaching the through hole 111. Hence, a distance D2 between the through hole 111 and the termination of the groove 113 preferably is in the range of the distance D1 in FIG. 1 between the through hole 111 and the recess 21.

Figure 7:
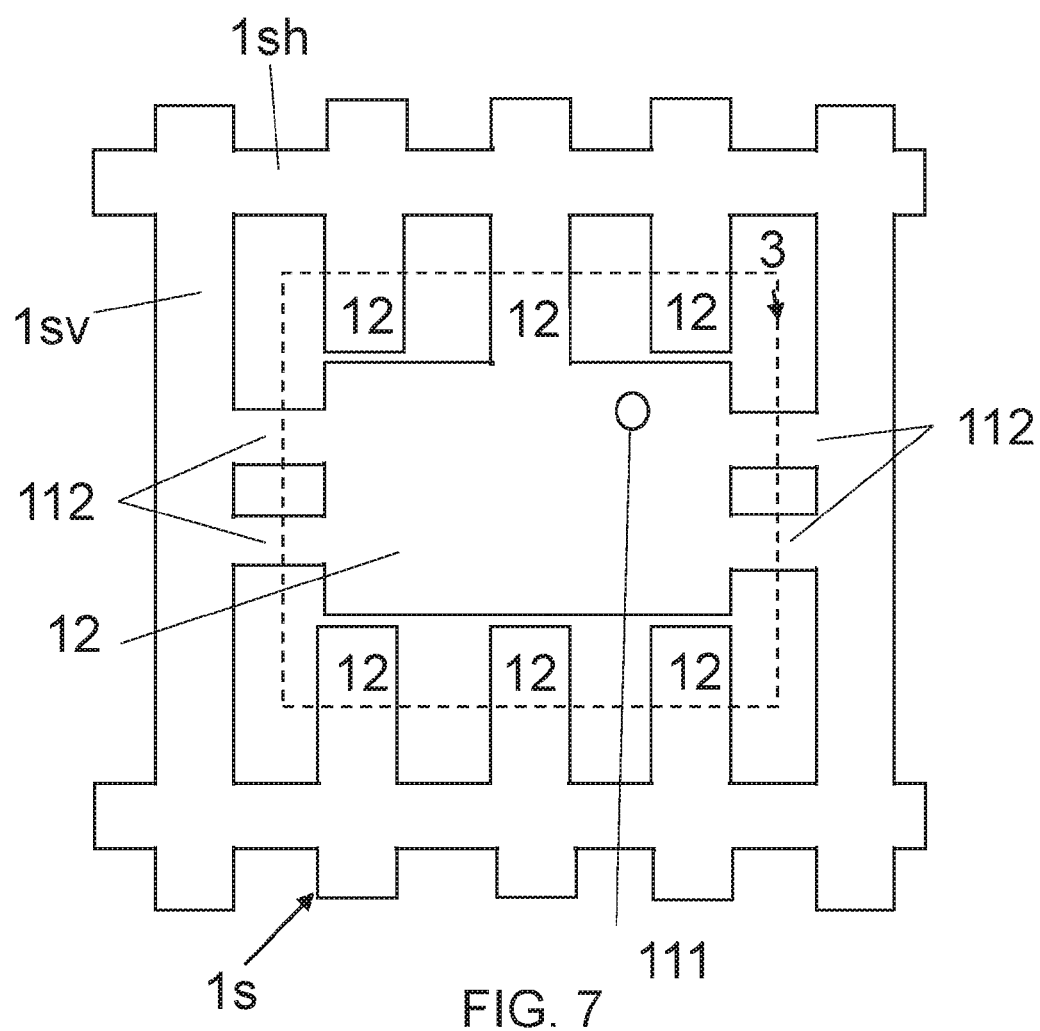
FIG. 7 a top view on a lead frame structure as used in an embodiment of a method for manufacturing a sensor package of the present invention.

In the FIGS. 1 and 2, there are lands 112 connecting to the die pad 11. This is owed to the die pad 11 representing a part of a lead frame structure 1 together with the contact pads 12. The lead frame structure 1 specifically is manufactured from a larger lead frame is as shown in FIG. 7. Accordingly, the contact pads 12 and the die pad 11 belong to the lead frame 1s which, for example, comprises horizontal leads 1sh from which the contact pads 12 depart. The die pad 11, instead, is connected by means of the lands 112 to vertical leads 1sv of the lead frame 1s. The sensor chip 2 is arranged on the die pad 11 in the way shown in FIG. 1. It is assumed, that the lead frame is in FIG. 7 further extends and provides multiple dies pads and contact pads connected to the various horizontal and vertical leads 1sh, 1sv. After having placed multiple sensor chips on the assigned die pads of the lead frame 1s, the sensor chips may electrically be connected to the assigned die pads, e.g. by means of wire bonds. Such arrangement then may be placed into a mold for providing an encapsulation for the sensor chips. In a first embodiment, the mold is designed such that protrusions are provided for defining future side walls of the sensor packages. In this variant, the shape of each individual sensor package is defined by the mold. In a different variant, this is not the case and the mold compound extends between the various sensor chips such that the shape of the individual sensor packages, and specifically their side walls, is defined by sawing the sensor packages from such molding block.

The shape of a resulting sensor package preferably is defined by the shape of the molding compound which is indicated by a dashed rectangle in FIG. 7.

FIG. 3 illustrates a cut through the sensor package of FIG. 1 along the lines A-A'. Presently, the sensor chip 2 comprises a semiconductor substrate and CMOS layers arranged on top of the substrate. The substrate may be etched or otherwise partially be removed from the back side bs such that the sensor chip 2 shows a recess 21 in its back side bs. As a result of building the recess 21, a thinned structure is generated which is also referred to as membrane 22. A sensitive layer 23 is arranged on or in the membrane 22 as well as a heater 24. In a specific embodiment, the sensitive layer 23 comprises a metal oxide layer which is to be heated by the heater 24 for enabling the sensing of chemical analytes. Hence, both the sensitive layer 23 and the heater 24 may be arranged on or in the membrane 22 above the recess 21. This arrangement is owed to a thermal insulation the membrane 22 provides which improves an accuracy of the measurement.

The sensor chip 2 is arranged on the front side FS of the die pad 11, with its back side bs and the recess 21 facing the die pad 11, and is attached thereto by an attachment layer 4. As a result, a cavity 5 is formed inside the sensor package. The through hole 111 connects the cavity 5 via the attachment layer 4 to the outside world. One or more of heat, pressure, contaminants may be transferred in the form of gas from the cavity 5 via the attachment layer 4 to the through hole 111 and escape from there.

The mold compound 3 encapsulates the sensor chip 2 except for an opening 31 towards the sensitive layer 23. In this embodiment, the opening 31 has a circular footprint which narrows towards the sensitive layer 23.

FIG. 4 illustrates a cut through the sensor package of FIG. 2 along the lines A-A'. Here, the groove 113 is visible in the die pad 11 which groove 113 terminates prior to reaching the through hole 111, and, on the other end connects to the cavity 5. Hence, one or more of heat, pressure, contaminants may be transferred in the form of gas from the cavity 5 via the groove 113 and the attachment layer 4 to the through hole 111 and escape from there.

FIG. 5 illustrates in its various diagrams the manufacturing of a sensor package according to a first embodiment of the present invention. According to diagram 5a), a dicing tape 6, e.g. made from olefin, is prepared with a die attach film 41 attached thereto. On the other hand, a wafer 2w comprising multiple sensor chips is prepared, preferably by having all the electronic functionality integrated therein, the heaters if any, the recess per sensor chip location, and possibly the sensitive elements. Such wafer 2w is then attached to the die attach film 41. According to diagram 5b), this arrangement is diced along the vertical lines. It is preferred that only the wafer 2w and the die attach film 41 are diced through while the dicing tape 6 is not, at least not completely. In the next step illustrated in diagram 5c), the sensor chip 2/die attach film 41 combinations are picked from the dicing tape 6, and are transferred to a lead frame 1s, and specifically on the individual die pads of the lead frame 1s. A release film between the dicing film 6 and the die attach film 41 may e.g. be an acrylic adhesive which is overcome by the picker. In a next step, this arrangement is placed in a mold, the mold is filled with a mold compound, and the resulting molded block shown in diagram 5e) is sawed along the vertical lines resulting in individual sensor packages. A sensitive element may be applied through an opening of the mold compound either prior to sawing or afterwards, if not yet applied to the wafer 2w.

Figure 6:
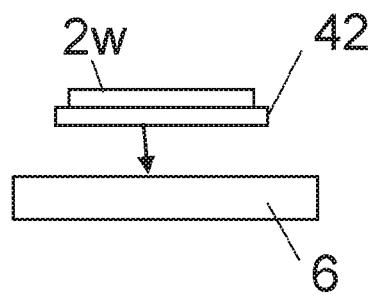
FIG. 6 a diagram illustrating a step of another method for manufacturing a sensor package according to an embodiment of the present invention.

In a different process of manufacturing a sensor package, the step illustrated in diagram 5a) is replaced by a step illustrated in FIG. 6. Accordingly, a coating 42 is attached to a back side of the prepared wafer 2w, while the dicing tape 6 does not comprise a die attach film as in diagram 5a). The back side coating may be implemented by printing a paste that is dried in the following. Preferably, the coating 42 is structured and does not extend over the area A2—see FIG. 1—and preferably does not extend over the area A3. In the following, the wafer 2w is attached by means of its back side coating 42 to the dicing tape 6. The further processing is equivalent to the process shown in diagrams 5b) to 5e).

While above there are shown and described embodiments of the invention, it is to be understood that the invention is not limited thereto but may otherwise be embodied and practiced within the scope of the following claims. In particular, it is emphasized that the method described in the various embodiments may include additional steps added or intermingled with the process steps described without leaving the scope of the method claims.

The invention claimed is:

1. A sensor package, comprising
a carrier comprising a through hole,
a sensor chip with a front side and a back side and a recess in the back side,
wherein, by means of an attachment layer, the sensor chip is attached to the carrier with its back side facing the carrier thereby defining a first area of the carrier the sensor chip rests on and a second area of the carrier facing the recess,
wherein the through hole is arranged in the first area of the carrier,
wherein the through hole is a venting hole for venting a cavity via the attachment layer, which cavity is formed between the sensor chip and the carrier by means of the recess,
said sensor package further comprising a groove in a front side of the carrier which front side faces the back side of the sensor chip,
wherein the groove extends from the cavity in direction to the through hole and terminates prior to reaching the through hole.

2. The sensor package of claim 1,
wherein the through hole is covered by the attachment layer.

3. The sensor package of claim 1,
comprising cut-outs in the attachment layer for the second area and for the through hole.

4. The sensor package of claim 1,
wherein a distance between the through hole and the termination of the groove is less than 250 µm.

5. The sensor package of claim 1,
wherein the attachment layer is a die attach film.

6. The sensor package of claim 1,
wherein the attachment layer is a film coated to the back side of the sensor chip.

7. The sensor package of claim 1, comprising
a layer sensitive to an environmental variable, which layer is arranged on or in a portion of the sensor chip above the recess,
a molding compound at least partially enclosing the sensor chip,
an opening in the molding compound providing access to the sensitive layer,
a lead frame structure including the carrier and contact pads for electrically contacting the sensor package from the outside, and
electrical connections between the sensor chip and the contact pads.

8. The sensor package of claim 1,
wherein for venting the cavity, the only way to get from the cavity to the through hole is through the attachment layer between the recess and the through hole.

9. Method for manufacturing the sensor package of claim 1, comprising
manufacturing a sensor chip with a front side, a back side and a recess in the back side,
manufacturing a through hole in a carrier, and a groove in a front side of the carrier,
attaching the sensor chip with its back side to the carrier by means of an attachment layer such that the through hole is located in a first area of the carrier the sensor chip rests on and a second area of the carrier faces the recess,
wherein the through hole is a venting hole for venting a cavity via the attachment layer, which cavity is formed between the sensor chip and the carrier by means of the recess,
wherein said front side of the carrier faces the back side of the sensor chip, and
wherein the groove extends from the cavity in direction to the through hole and terminates prior to reaching the through hole.

10. Method according to claim 9, comprising
manufacturing the sensor chip including the recess in a wafer together with multiple other sensor chips,
providing a dicing tape with a die attach film arranged thereon,
placing the wafer with its back side onto the die attach film,
dicing the wafer including the die attach film into individual sensor chips,
picking a sensor chip of the individual sensor chips including the die attach film from the dicing tape and attaching the sensor chip with the die attach film as attachment layer onto the carrier.

11. Method according to claim 9, comprising
manufacturing the sensor chip including the recess in a wafer together with multiple other sensor chips,
attaching a coating to a back side of the wafer,
placing the wafer with the back side coating onto a dicing tape,
dicing the wafer including the back side coating into individual sensor chips,
picking a sensor chip of the individual sensor chips including the back side coating from the dicing tape and attaching the sensor chip with the back side coating as attachment layer onto the carrier.

12. Method according to claim 10,
wherein the sensor package includes a sensitive layer sensitive to an environmental variable, which layer is arranged on or in a portion of the sensor chip above the recess,
wherein the carrier is integrated in a lead frame providing carriers for multiple sensor chips which carriers are interconnected with each other,
wherein multiple sensor chips are attached to assigned carriers of the lead frame by means of the die attach film respectively,
wherein a molding compound is applied to the lead frame thereby at least partially enclosing each sensor chip and providing an opening in the molding compound of each sensor chip for granting access to the sensitive layer, and
dicing the molded lead frame into individual sensor packages.

13. A sensor package, comprising
a carrier comprising a through hole,
a sensor chip with a front side and a back side and a recess in the back side,
wherein, by means of an attachment layer, the sensor chip is attached to the carrier with its back side facing the carrier thereby defining a first area of the carrier the sensor chip rests on and a second area of the carrier facing the recess,
wherein the through hole is arranged in the first area of the carrier,
said sensor package further comprising
a layer sensitive to an environmental variable, which layer is arranged on or in a portion of the sensor chip above the recess, and
a heater for heating the sensitive layer.

* * * * *